United States Patent [19]
Takahashi

[11] 3,932,426
[45] Jan. 13, 1976

[54] 3-[1-HYDROXY-2-(3- OR 4-HYDROXYPIPERIDINO)ETHYL]-5-PHENYLISOXAZOLE

[75] Inventor: Shiro Takahashi, Shita, Japan

[73] Assignee: Shionogi & Co., Ltd., Dosho, Japan

[22] Filed: Aug. 12, 1974

[21] Appl. No.: 496,858

[30] Foreign Application Priority Data
Aug. 23, 1973 Japan.................................. 48-94563
Aug. 23, 1973 Japan.................................. 48-94565

[52] U.S. Cl. ......... 260/293.67; 260/307 H; 424/267
[51] Int. Cl.². ...................................... C07D 211/40
[58] Field of Search .............................. 260/293.67

[56] References Cited
OTHER PUBLICATIONS
J. Med. Chem. 10: 411–418 (1967), Kano et al.

*Primary Examiner*—Sherman D. Winters
*Attorney, Agent, or Firm*—Wenderoth, Lind & Ponack

[57] ABSTRACT

3-[1-Hydroxy-2-(3- or 4-hydroxypiperidino)ethyl]-5-phenylisoxazole synthesized from 3-(1,2-epoxyethyl)-5-phenylisoxazole or 3-(1-hydroxy-2-active group-substituted ethyl)-5-phenylisoxazole with 3- or 4-hydroxypiperidine, or 3-(3- or 4-hydroxypiperidino)acetyl-5-phenylisoxazole or 3-(3- or 4-ketopiperidino)acetyl-5-phenylisoxazole by reduction showing strong analgesic and anti-inflammatory activities with low toxicity.

3 Claims, No Drawings

3-[1-HYDROXY-2-(3- OR 4-HYDROXYPIPERIDINO)ETHYL]-5-PHENYLISOXAZOLE

This invention relates to novel isoxazole derivatives. Further, it relates to processes for their preparation.

The said isoxazole derivatives may be represented by the following formula:

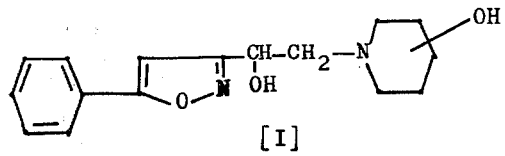

[I]

wherein the hydroxy group on the piperidine ring is located at its 3 or 4 position.

More particularly, the isoxazole compounds to which the present invention concerns, are 3-[1-hydroxy-2-(3-hydroxypiperidino)-ethyl]-5-phenylisoxazole and 3-[1-hydroxy-2-(4-hydroxypiperidino)-ethyl]-5-phenylisoxazole.

The said isoxazole derivatives of the formula [I] are novel and have been discovered to show strong analgesic and anti-inflammatory activities.

Accordingly, a basic object of this invention is to provide novel isoxazole derivatives of the formula [I]. More precisely, it is to provide 3-[1-hydroxy-2-(3- or 4-hydroxypiperidino)ethyl]-5-phenylisoxazole. Another object of the invention is to provide isoxazole derivatives showing strong analgesic and anti-inflammatory activities with low toxicity. A further object of the invention is to provide processes for preparing the novel isoxazole derivatives. These and other objects and manners in which they are accomplished will become apparent to those conversant with the art from the following descriptions.

The novel isoxazole derivatives of the formula [I] may be prepared in various ways of which the general aspect may be illustrated by the following scheme:

wherein X represents active functional group and the hydroxy group or the oxo group on the piperidine ring is located at its 3 or 4 position.

According to the present invention, the compounds of the formula [I] can be produced by some different methods, which are illustrated in detail below, respectively.

a. Preparation from 3-(1,2-epoxyethyl)-5-phenylisoxazole [II] with hydroxypiperidine 3-[1-Hydroxy-2-(3- or 4-hydroxypiperidino)ethyl]-5-phenylisoxazole can be prepared by heating 3-(1,2-epoxyethyl)-5-phenylisoxazole with 3- or 4-hydroxypiperidine. Generally, the reaction may be executed at a temperature ranging from about 20°C to about 200°C for about 0.2 to about 60 hours under ordinary (atmospheric) pressure, while the reaction conditions may be varied depending on the properties of the starting materials. The reaction solvent is not necessarily required, but may be selected from, for example, aromatic hydrocarbons (e.g., benzene, toluene, xylene), aliphatic hydrocarbons (e.g., pentane, hexane, heptane), ethers (e.g., ether, tetrahydrofuran, dioxane), alcohols (e.g., methanol, ethanol, propanol), halogenohydrocarbons (e.g., chloroform, carbon tetrachloride), dimethylsulfoxide, dimethylformamide and the like. They can be employed solely or as a mixture in consideration of the solubility of the starting compounds as well as other reaction conditions employed. Further, by use of an excess of the hydroxypiperidine the reaction can be effected without other solvent.

b. Preparation from 3-(1-hydroxy-2-active group-substituted ethyl)-5-phenylisoxazole [III] with hydroxypiperidine 3-[1-Hydroxy-2-(3- or 4-hydroxypiperidino)ethyl]-5-phenylisoxazole can also be prepared by heating 3-(1-hydroxy-2-active group-substituted ethyl)-5-phenylisoxazole with 3- or 4-hydroxypiperidine. The active group means a functional group which is capable of reacting with a hydroxypiperidine to form compound [I]. They are, for example, halogen (e.g., iodine, bromine, chlorine) and arenesulfonyloxy group (e.g.,

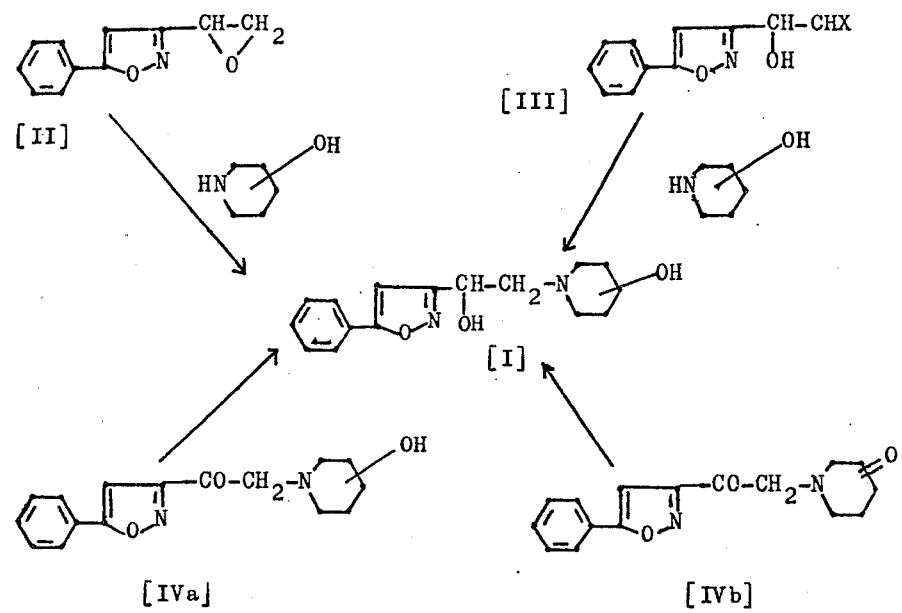

benzenesulfonyloxy, tosyloxy). The reaction may be carried out in the same manner as described in the previous method (a). That is the compound [III] is heated with 3- or 4-hydroxypiperidine optionally in the presence of a solvent selected from those described above. Generally, the reaction may be executed at a temperature ranging from about 20°C to about 200°C for about 0.2 to about 60 hours under ordinary (atmospheric) pressure, while the reaction conditions may be varied depending on the properties of the starting materials. In the present reaction, the starting compound [III] is converted to compound [I] via compound [II].

c. Preparation from 3- (3- or 4-hydroxypiperidino)-acetyl-5-phenylisoxazole [IVa] or 3-(3 - or 4-ketopiperidino)-acetyl-5-phenylisoxazole [IVb]

The objective compound 3-[1-hydroxy-2-(3- or 4-hydroxypiperidino) ethyl]-5-phenylisoxazole can be prepared by reducing 3-(3- or 4-hydroxypiperidino)acetyl-5-phenylisoxazole [IVa] or 3-(3- or 4-ketopiperidino)acetyl-5-phenylisoxazole ]IVb]. The reduction is executed with a metal hydride. Examples of the metal hydride include alkali metal borohydrides (e.g., sodium borohydride, lithium borohydride, potassium borohydride), alkali metal aluminum hydrides (e.g., lithium aluminum hydride, sodium aluminum hydride), sodium cyanoborohydride, sodium bis(2-methoxyethoxy)aluminum hydride and sodium diethylaluminum hydride. The reduction may be carried out in a conventional manner. Generally, it is executed at a temperature ranging from about 0°C to about 100°C under ordinary (atmospheric) pressure. The reaction solvent may be selected from, for example, water, alcohols (e.g., methanol, ethanol, propanol, ethyleneglycol), ethers (e.g., ether, dioxane, tetrahydrofuran) and the like in consideration of the solubility of the starting compound as well as the properties of the reducing agent employed.

Both compound [IVa] and compound [IVb] can give the objective compound [I].

Thus obtained compound [I] can be converted into their suitable acid addition salts in conventional manner in accordance with requirement of the separation, purification or formulation. Compound [I] is treated with an acid such as hydrochloric, hydrobromic, hydroiodic, sulfuric, nitric, phosphoric, thiocyanic, carbonic, acetic, propionic, oxalic, citric, tartaric, succinic, maleic, salicylic, benzoic, phthalic and palmitic acid in a suitable solvent such as water, methanol, ethanol, benzene and toluene. There are thus produced hydrochloride, hydrobromide, hydroiodide, sulfate, nitrate, phosphate, thiocyanate, carbonate, acetate, propionate, oxalate, citrate, tartarate, succinate, malate, salicylate, benzoate, phthalate, palmitate and the like.

Besides, compound [I] is an optically active compound and may be resolved into d-isomer and l-isomer. The optical resolution can be executed in a conventional manner and both isomers possess pharmacological activities. Therefore, they can be used as a mixture or in singles depending on the therapeutical requirement.

Previously, 3-(1-hydroxy-2-piepridinoethyl)-5-phenylisoxazole was found that is useful as a medicament having anti-inflammatory and analgesic activities. The 3-[1-hydroxy-2-(3- or 4-hydroxy-piperidino) ethyl]-5-phenylisoxazole of the present invention, however, are structurally characterized by the presence of a hydroxy group on its piperidine nucleus, when compared with the above-cited compound synthesized previously. It has now been discovered that the compound [I] shows excellent anti-inflammatory and analgesic activities with a low toxicity and are superior to the above-cited 3-(1-hydroxy-2-piperidinoethyl )-5-phenylisokazole particularly in low toxicity.

Further, non-toxic acid addition salts of compound [I] provided by the present invention also show similarly distinguished pharmaceutically properties. The compound [I] and pharmaceutically acceptable non-toxic salts are useful in the treatment of various rheumatic diseases, inflammations or pains solely or in combination with a solid or liquid pharmaceutical carrier. Practical examples of suitable pharmaceutical preparations of the compound [I] and its salts are tablets, capsules, pills, granules, powders, suppositories, or injectable solutions.

The following are given solely for the purpose of illustration and not to be construed as limitation of the present invention.

Example 1 a. A mixture of 3-(1,2-epoxyethyl)-5-phenylisoxazole (580 mg) and 4-hydroxypiperidine (625 mg) is stirred for 0.5 hour at 80°C and then the mixture is subjected to a column chromatography using silica gel to give 3-[1-hydroxy-2-(4-hydroxypiperidino ) ethyl]-5-phenylisoxazole (450 mg). Recrystallization from ethyl acetate-hexane gives colorless prisms (259 mg). M. p. 117–119°C.

Anal. Calcd. for $C_{16}H_{20}N_2O_3$: C, 66.64; H, 6.99; N, 9.72. Found: C, 66.38; H, 7.12; N, 9.58.

b. A mixture of 3-(1-hydroxy-2-bromoethyl)-5-phenylisoxazole (268 mg) and 4-hydroxypiperidine (121 mg) is dissolved in a mixture (4 ml) of 99% ethanol and benzene (1:1). To the solution is added sodium hydrogen carbonate (168 mg) and stirred at 70°C for 5 hours. After removal of the solvent, the residue is subjected to a column chromatography (silica gel,) eluted with a mixture of methylene chloride and methanol, and the crude crystals collected are recrystallized from ethyl acetate to give 3-[1-hydroxy-2-(4-hydroxypiperidino)ethyl]-5-phenylisoxazole (180 mg) as colorless prisms melting at 117–119°C.

c. To a solution of 3-(4-hydroxypiperidino)acetyl-5-phenylisoxazole (25 mg) in ether (10 ml) is added a solution of sodium borohydride (15 mg) in ethanol (1.0 ml) with stirring and then the mixture is stirred for 1 hour. After being cooled, the mixture is acidified with a dilute hydrochloric acid and evaporated under reduced pressure. To the residue is added water and the solution is made alkaline with an aqueous solution of potassium hydroxide, then extracted with chloroform. After removal of the solvent, the residue is subjected to a chromatography using silica gel to give crystalline 3-[1-hydroxy-2-(4-hydroxypiperidino) ethyl]-5-phenylisoxazole. Recrystallization from a mixture of ethyl acetate and hexane gives colorless prisms (20 mg) melting at 117–119°C.

EXAMPLE 2

(a) A mixture of 3-(1,2-epoxyethyl)-5-phenylisoxazole (1.05 g) and 3-hydroxypiperidine (1.13 g) is heated at 70°C for 20 minutes and then chromatographed on silica gel to give 3-[1-hydroxy-2-(3-hydroxypiperidino)ethyl]-5-phenylisoxazole (1.25 g). To a suspension of the compound in water (6.5 ml) is added 60% perchloric acid (516 ml), the precipitate is collected by filtration, and recrystallized from a mixture of 99% ethanol (2 ml) and ethyl acetate (8 ml) to give the perchlorate which melts at 151°–153°C. The perchlorate is suspended in aqueous sodium hydroxide solution and extracted with methylene chloride. After being dried with sodium sulfate, the extract is evaporated to give 3-[1-hydroxy-2-(3-hydroxypiperidino) ethyl]-5-phenylisoxazole (544 mg). Recrystallization from a mixture of ethyl acetate and hexane gives colorless prisms (388 mg) melting at 94°–96°C.

Anal. Calcd. for $C_{16}H_{20}N_2O_3$: C, 66.64; H, 6.99; N, 9.72. Found: C, 66.76; H, 6.74; N, 9.57.

b. 3-(3-Hydroxypiperidino)acetyl-5-phenyl-isoxazole (1.05 g) is treated in the same manner as in Example 1 (c) to give 3-[1-hydroxy-2-(3-hydroxypiperidino)ethyl]-5-phenylisoxazole (0.28 g). Recrystallization from a mixture of ethyl acetate and hexane gives colorless prisms melting at 94°–96°C.

What we claim is:

1. A member selected from the compounds of the formula:

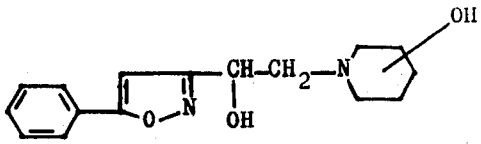

wherein the hydroxy group on the piperidine ring is located at its 3 or 4 position.

2. A compound according to claim 1, namely 3-[1-hydroxy-2-(4-hydroxypiperidino) ethyl]-5-phenylisoxazole.

3. A compounding according to claim 1, namely 3-[1-hydroxy-2-(3-hydroxypiperidino)ethyl]ethyl]-5-phenylisoxazole.

* * * * *